US012697286B2

(12) United States Patent (10) Patent No.: US 12,697,286 B2
Li et al. (45) Date of Patent: Aug. 4, 2026

(54) ZIRCONIA-BASED ANTIBACTERIAL DENTURE MATERIAL AND PREPARATION METHOD THEREOF

(71) Applicant: SHENZHEN YURUCHENG DENTAL MATERIALS CO., LTD., Shenzhen (CN)

(72) Inventors: Zongyu Li, Shenzhen (CN); Wei Liu, Shenzhen (CN); Yu Zhang, Shenzhen (CN); Jianjun Liu, Shenzhen (CN)

(73) Assignee: SHENZHEN YURUCHENG DENTAL MATERIALS CO., LTD., Shenzhen (CN)

( * ) Notice: Subject to any disclaimer, the term of this patent is extended or adjusted under 35 U.S.C. 154(b) by 426 days.

(21) Appl. No.: 18/483,079

(22) Filed: Oct. 9, 2023

(65) Prior Publication Data

US 2024/0156688 A1 May 16, 2024

(30) Foreign Application Priority Data

Nov. 11, 2022 (CN) .......................... 202211412647.6

(51) Int. Cl.
| | |
|---|---|
| *A61K 6/818* | (2020.01) |
| *A61C 13/083* | (2006.01) |
| *A61K 6/17* | (2020.01) |
| *C04B 35/48* | (2006.01) |
| *C04B 35/63* | (2006.01) |
| *C04B 35/645* | (2006.01) |

(52) U.S. Cl.
CPC ............ *A61K 6/818* (2020.01); *A61C 13/083* (2013.01); *A61K 6/17* (2020.01); *C04B 35/48* (2013.01); *C04B 35/63* (2013.01); *C04B 35/645* (2013.01)

(58) Field of Classification Search
CPC ........ A61K 6/818; A61K 6/17; A61C 13/083; C04B 35/48; C04B 35/63; C04B 35/645
See application file for complete search history.

(56) References Cited

U.S. PATENT DOCUMENTS

| | | |
|---|---|---|
| 10,723,657 B2 | 7/2020 | Perie |
| 2013/0014671 A1 | 1/2013 | Tzeng |

FOREIGN PATENT DOCUMENTS

| | | |
|---|---|---|
| CN | 1627931 A | 6/2005 |
| CN | 106495681 A | 3/2017 |
| CN | 108136065 A | 6/2018 |
| CN | 111039670 A | 4/2020 |

(Continued)

OTHER PUBLICATIONS

First Office Action issued in counterpart Chinese Patent Application No. 202211412647.6, dated Apr. 29, 2023.

(Continued)

*Primary Examiner* — Crystal J Lee
(74) *Attorney, Agent, or Firm* — Westbridge IP LLC

(57) ABSTRACT

Disclosed are a zirconia-based antibacterial denture material and a preparation method thereof. The zirconia-based antibacterial denture material includes components with the following mass parts: 75 to 80 parts of zirconium oxide, 2 to 5 parts of nanosized silver oxide, 3 to 5 parts of nanosized zinc oxide, 1 to 3 parts of nanosized lanthanum oxide, 1 to 3 parts of nanosized yttrium oxide, 1 to 2 parts of cerium oxide, and 1 to 2 parts of size control agent. The zirconia-based antibacterial denture material has good antibacterial effect and high strength.

10 Claims, 1 Drawing Sheet

(56)          References Cited

FOREIGN PATENT DOCUMENTS

| CN | 112250438 A | * | 1/2021 | ............. | A61K 6/818 |
| CN | 114368966 A | | 4/2022 | | |
| JP | H0833650 A | | 2/1996 | | |

OTHER PUBLICATIONS

Grant Notification issued in counterpart Chinese Patent Application No. 202211412647.6, dated Sep. 27, 2023.
European Search Report issued in counterpart European Patent Application No. EP 23200343.4, dated Mar. 7, 2024.

* cited by examiner

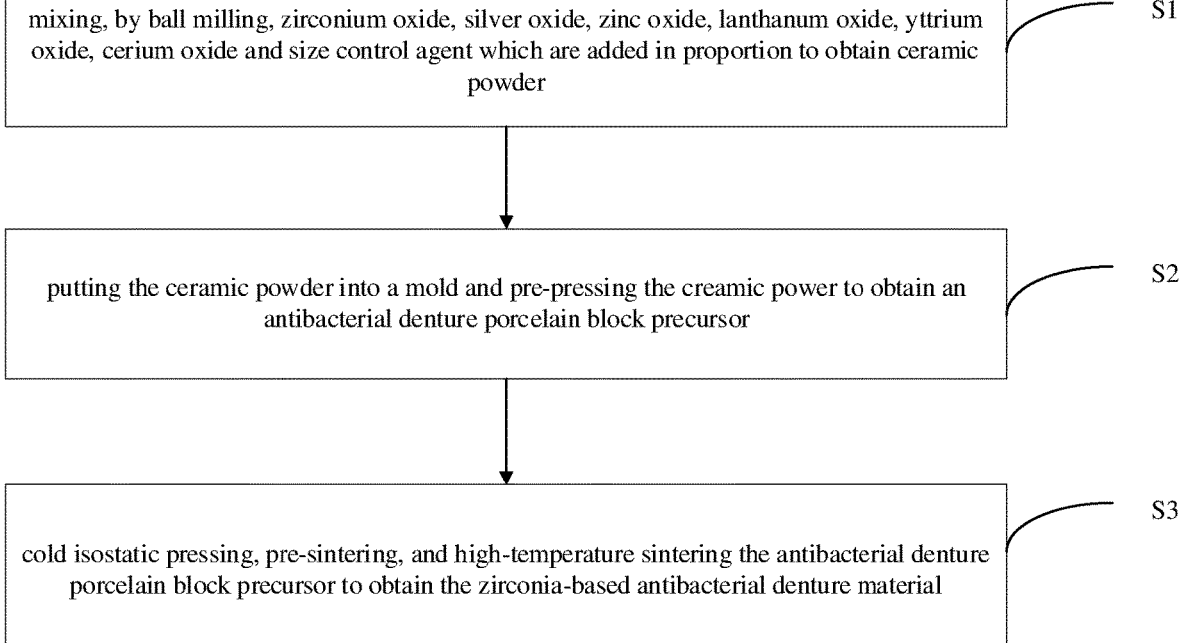

mixing, by ball milling, zirconium oxide, silver oxide, zinc oxide, lanthanum oxide, yttrium oxide, cerium oxide and size control agent which are added in proportion to obtain ceramic powder     S1 putting the ceramic powder into a mold and pre-pressing the creamic power to obtain an antibacterial denture porcelain block precursor     S2 cold isostatic pressing, pre-sintering, and high-temperature sintering the antibacterial denture porcelain block precursor to obtain the zirconia-based antibacterial denture material     S3

ZIRCONIA-BASED ANTIBACTERIAL DENTURE MATERIAL AND PREPARATION METHOD THEREOF

CROSS-REFERENCE TO RELATED APPLICATIONS

This application claims priority to Chinese Patent Application No. 202211412647.6, filed on Nov. 11, 2022, the entire contents of which are incorporated herein by reference.

TECHNICAL FIELD

The present application relates to the technical field of denture, in particular to a zirconia-based antibacterial denture material and a preparation method thereof.

BACKGROUND

Dentures, commonly referred to as "false teeth", are a general term in medicine for the prosthetic restorations made to replace partially or completely missing teeth in the upper and lower jaws. Dentures are categorized into two types: removable and fixed. Fixed dentures cannot be removed and worn by patients themselves, while removable dentures can be easily taken in and out by the patients.

For breaking the balance of the original oral ecological environment, the dentures as foreign bodies in the oral cavity, are more likely to hide dirt than natural teeth. If they are not cleaned in time, plaque will form on the surfaces of the dentures and natural teeth. If acid bacteria remain on the enamel surface for a long time, it can cause oral diseases such as dental caries, gingivitis, periodontal disease, and denture stomatitis. In more severe cases, other pathogenic bacteria attached to the dentures may enter a respiratory system through an oropharynx. There is also a risk of causing infectious diseases such as bacterial pneumonia. Therefore, there is an urgent need for antibacterial denture materials with antibacterial properties to solve the problem of existing dentures that break the oral ecological balance and cause oral diseases after wearing them.

In the existing technology, two methods are usually used for antibacterial treatment: denture surface treatment and self-treatment. The former is to change the charge on the surface of the denture or form a polyelectrolyte multilayer film, etc. However, during the use of this method, due to long-term wear of the denture, its antibacterial properties can be reduced. The latter is to add antibacterial agents such as zinc oxide during the denture molding process. However, since a band gap of zinc oxide is 3.3 ev, it can only absorb ultraviolet light with a wavelength less than 385 nm, and cannot exert its antibacterial effect very well when used in visible light or dark environments. Thus, the antibacterial effect of this type of antibacterial denture also needs to be improved.

SUMMARY

The present application provides a zirconia-based antibacterial denture material and a preparation method thereof. The zirconia-based antibacterial denture material has a good antibacterial effect and high strength.

In order to achieve the above technical objective, the present application adopts the following technical solutions.

The present application provides a zirconia-based antibacterial denture material, including components with the following mass parts: 75 to 80 parts of zirconium oxide, 2 to 5 parts of nanosized silver oxide, 3 to 5 parts of nanosized zinc oxide, 1 to 3 parts of nanosized lanthanum oxide, 1 to 3 parts of nanosized yttrium oxide, 1 to 2 parts of cerium oxide, and 1 to 2 parts of size control agent.

In some embodiments, the size control agent is calcium silicate.

In some embodiments, a ratio of a sum of masses of the silver oxide and the zinc oxide to the mass of the yttrium oxide is between 5 to 0.5 and 5 to 1.

In some embodiments, a particle size of the zirconium oxide is less than or equal to 30 nm.

The present application further provides a preparation method of a zirconia-based antibacterial denture material, including:

S1, weighing zirconium oxide, silver oxide, zinc oxide, lanthanum oxide, yttrium oxide, cerium oxide and size control agent in proportion, and mixing by ball milling, to obtain ceramic powder;

S2, putting the ceramic powder into a mold and pre-pressing the ceramic power to obtain an antibacterial denture porcelain block precursor;

S3, performing cold isostatic pressing, pre-sintering, and high-temperature sintering on the antibacterial denture porcelain block precursor to obtain the zirconia-based antibacterial denture material.

In some embodiments, a pressure of the cold isostatic pressing is 100 MPa to 300 MPa, and a pressure holding time is 60 seconds to 600 seconds.

In some embodiments, a pressure of the pre-pressing is 5 MPa to 50 MPa, and a pressure holding time is 10 seconds to 60 seconds.

In some embodiments, a final temperature of the pre-sintering is 800° C. to 1000° C., a heating rate is 10° C./min to 15° C./min and a temperature holding time is 1 hour to 5 hours.

In some embodiments, a final temperature of the high-temperature sintering is 1400° C. to 1550° C., a heating rate is 1° C./min to 10° C./min and a temperature holding time is 1 hour to 5 hours.

In some embodiments, a process of the high-temperature sintering is performed in a magnetic field environment.

The beneficial effects of the present application are as follows: in this technical solution, by mixing and sinthering zinc oxide, lanthanum oxide, and cerium oxide, the zirconia-based antibacterial denture material has excellent antibacterial properties, and can effectively inhibit *Escherichia coli* and *Staphylococcus aureus* for a long time. The addition of lanthanum oxide, yttrium oxide, cerium oxide and size control agents in the zirconia-based antibacterial denture material overcomes the defect of reducing the mechanical properties of the zirconium oxide ceramic caused by adding antibacterial materials, such as zinc oxide and silver oxide. The preparation method of a zirconia-based antibacterial denture material is simple and fast, and by adjusting the pressure and sintering parameters, it can prevent "porcelain chipping" during the molding process.

BRIEF DESCRIPTION OF THE DRAWINGS

In order to more clearly illustrate the technical solutions in the embodiments of the present application or in the related art, drawings in the embodiments or in the related art will be briefly described below. Obviously, the drawings in the following description are only some embodiments of the present application. Other drawings can be obtained by those skilled in the art according to the structures shown in the drawings without creative efforts.

FIG. 1 is a schematic flowchart of a preparation method for a zirconia-based antibacterial denture material according to some embodiments of the present application.

The realization of the purpose, functional characteristics and advantages of the present application will be further described with reference to the attached drawings in combination with embodiments.

DETAILED DESCRIPTION OF THE EMBODIMENTS

In order to clarify the purpose, technical solutions and advantages of the present application, the present application will be further described in detail below in conjunction with embodiments. It should be understood that the specific embodiments described here are only used to explain the present application and are not intended to limit the present application.

As a conventional antibacterial material, zinc oxide has been generally recognized in antibacterial ceramics, but it is rarely used in denture ceramics. The reason is that a band gap of zinc oxide is 3.3 ev and can only absorb ultraviolet light with a wavelength less than 385 nm. However, the use environment of dentures is mostly hot, humid and dark or visible light conditions. Therefore, zinc oxide cannot fully exert its antibacterial properties in denture materials. Although silver oxide is also a conventional antibacterial material, its utility as a denture material is not applicable, since its stability and durability are poor and the denture material needs to be used for a long time. Furthermore, zirconia-based denture materials need to have excellent mechanical properties to prevent denture damage, and adding soft metal-based oxides such as silver oxide, zinc oxide, copper oxide and other substances can reduce their wear resistance. Therefore, it is necessary to provide a zirconia-based antibacterial denture material that can not only ensure the wear resistance of zirconia-based dentures but also improve their antibacterial performance.

Based on this, the present application is proposed.

The present application provides a zirconia-based antibacterial denture material, including components with the following mass parts: 75 to 80 parts of zirconium oxide, 2 to 5 parts of nanosized silver oxide, 3 to 5 parts of nanosized zinc oxide, 1 to 3 parts of nanosized lanthanum oxide, 1 to 3 parts of nanosized yttrium oxide, 1 to 2 parts of cerium oxide, 1 to 2 parts of size control agent.

In this technical solution, in order to improve the absorption of visible light by zinc oxide, other modified ions can be doped to change and narrow the band gap of zinc oxide, while increasing surface defects to improve the photocatalytic activity of zinc oxide, and thereby enhancing the antibacterial ability. After sintering, cerium and lanthanum in the zirconia-based antibacterial denture material synergistically promote the formation of zinc oxide in the nanosized wurtzite crystal form to reduce a bandgap width value, thereby improving its photocatalytic antibacterial activity. At the same time, lanthanum oxide itself also has antibacterial properties and can cooperate with other antibacterial substances to enhance the antibacterial rate and broad spectrum. Cerium oxide can also form a reinforced composite material with zirconium oxide to improve the strength of the material. Meanwhile, lanthanum oxide has a strong restriction effect on the grains growth of zinc oxide. Under the restriction effect, more silver can enter the zinc oxide crystal lattice to act as an electron acceptor and change the semiconductor energy level, causing zinc oxide to produce more antibacterial active centers, and zinc oxide with a special structure in the product has been proven to produce reactive oxygen species such as hydroxyl radicals, superoxide anions, hydrogen peroxide and other reactive oxygen species to kill bacteria. Zinc oxide do not change or decrease during this process. At the same time, nano-effects in the local or hybrid structures of special structure zinc oxide antibacterial agent with the special structure, as well as the synergistic effect of trace amounts of zinc ions within a controlled range, can help to enhance their bactericidal performance. The bactericidal mechanism is enhanced through the synergy of active oxygen effects, nano-effects, ionic effects, etc., and ultimately improve the antibacterial ability of zirconia-based denture materials.

In addition, lanthanum oxide can increase the sintering density of zirconia-based ceramics, but its sintering temperature is relatively high. Therefore, adding yttrium oxide reduces its sintering temperature and improves its sintering performance. At the same time, lanthanum oxide and yttrium oxide can synergistically enhance the strength of zirconia-based ceramics, and improve its wear resistance. Although yttrium oxide also has this function, the concentration of single-component yttrium oxide is too high, which is bad for mechanical properties. That's why lanthanum oxide and yttrium oxide are added together to improve the strength of denture materials. Therefore, it's necessary for yttrium oxide and lanthanum oxide to work together to increase the density and strength of the material to form a dense and smooth denture.

Among the above components, the size control agent is calcium silicate to control the excessive expansion of the material during the molding process and to prevent the occurrence of pores or porcelain chipping.

A ratio of a sum of the masses of silver oxide and zinc oxide to the mass of yttrium oxide is between 5:0.5 and 5:1. Excessive yttrium oxide can reduce the mechanical strength of the denture material, but within this range, it can be ensured that the strength of the denture material cannot decrease due to the addition of sliver oxide or zinc oxide.

The particle size of zirconium oxide is less than or equal to 30 nm. As the base material, the zirconium oxide used is nanosized zirconium oxide. This particle size is beneficial to the mixing uniformity of the material during the preparation process.

The present application further provides a preparation method of a zirconia-based antibacterial denture material, as shown in FIG. 1, including the following steps:

S1, weighing zirconium oxide, silver oxide, zinc oxide, lanthanum oxide, yttrium oxide, cerium oxide and size control agent in proportion, and mixing by ball milling to obtain ceramic powder;

S2, putting the ceramic powder into a mold and pre-pressing the ceramic power to obtain an antibacterial denture porcelain block precursor; and S3, performing cold isostatic pressing, pre-sintering, and high-temperature sintering treatment on the antibacterial denture porcelain block precursor in sequence to obtain the zirconia-based antibacterial denture material.

A pressure of the cold isostatic pressing is 100 MPa to 300 MPa. In some embodiments, the pressure of the cold isostatic pressing is 200 MPa to 300 MPa, with a pressure holding time of 60 seconds to 600 seconds; and a pre-pressing pressure is 5 MPa to 50 MPa. In some embodiments, the pre-pressing pressure is 40 MPa to 50 MPa, with a pressure holding time of 10 seconds to 60 seconds.

The final temperature of the pre-sintering is 800° C. to 1000° C., with a heating rate of 10° C./min to 15° C./min. In some embodiments, the heating rate is 10° C./min to 15° C./min and a temperature holding time is 1 hour to 5 hours. The final temperature of the high-temperature sintering is 1400° C. to 1550° C., with a heating rate of 1° C./min to 10° C./min. In some embodiments, the heating rate is 1° C./min to 3° C./min and the temperature holding time is 1 hour to 5 hours. Under this program, the sintering efficiency can be guaranteed and collapsing or cracking of the porcelain caused by rapid heating can be prevented.

In some embodiments, the high-temperature sintering process is carried out in a magnetic field environment, which can improve the uniform distribution of each material component, not only enhancing the effective antibacterial performance in all directions of the material without leaving any hygienic dead corners, but also improving the mechanical strength of the material.

The present application will be further described below through specific embodiments.

Embodiments 1 to 7

A zirconia-based antibacterial denture material, including the following components: zirconium oxide, nanosized silver oxide, nanosized zinc oxide, nanosized lanthanum oxide, nanosized yttrium oxide, cerium oxide and calcium silicate. The formulation of components of the zirconia-based antibacterial denture material of embodiments 1-7 is shown in Table 1.

temperature of the high-temperature sintering is 1400° C. to 1550° C., a heating rate is 1° C./min and a temperature holding time is 1 hour to 5 hours, to obtain the zirconia-based antibacterial denture material.

Embodiment 8

A zirconia-based antibacterial denture material, including the following components: 75 parts of zirconium oxide, 5 parts of nanosized silver oxide, 5 parts of nanosized zinc oxide, 3 parts of nanosized lanthanum oxide, 2 parts of nanosized yttrium oxide, 2 parts of cerium oxide and 2 parts of calcium silicate.

The preparation steps of the zirconia-based antibacterial denture material are as follows:

S1, weighing zirconium oxide, silver oxide, zinc oxide, lanthanum oxide, yttrium oxide, cerium oxide and size control agent in proportion, and mixing by ball milling, to obtain ceramic powder;

S2, putting the ceramic powder into a mold and pre-pressing the ceramic power to obtain an antibacterial denture porcelain block precursor, wherein the pre-pressing pressure is 5 MPa to 50 MPa and the pressure holding time is 10 seconds to 60 seconds; and S3, performing the cold isostatic pressing the antibacterial denture porcelain block precursor, the pressure of the cold isostatic pressing is 100 MPa to 300 MPa and the pressure holding time is 60 seconds to 600 seconds; then performing the pre-sintering on the antibacterial denture porcelain block precursor, the final temperature

TABLE 1 the formulation of components of the zirconia-based antibacterial denture material of embodiments

| | Zirconium oxide | Nanosized silver oxide | Nanosized zinc oxide | Nanosized lanthanum oxide | Nanosized yttrium oxide | Cerium oxide | Calcium silicate |
|---|---|---|---|---|---|---|---|
| Embodiment 1 | 75 | 5 | 5 | 3 | 2 | 1 | 2 |
| Embodiment 2 | 75 | 5 | 5 | 3 | 2 | 1.5 | 2 |
| Embodiment 3 | 75 | 5 | 5 | 3 | 2 | 2 | 2 |
| Embodiment 4 | 75 | 5 | 5 | 2 | 2 | 2 | 2 |
| Embodiment 5 | 75 | 5 | 5 | 1 | 2 | 2 | 2 |
| Embodiment 6 | 80 | 5 | 5 | 1 | 3 | 2 | 1 |
| Embodiment 7 | 80 | 2 | 3 | 3 | 2 | 2 | 1 |

The zirconia-based antibacterial denture material is prepared according to the components in Table 1, the preparation steps are as follows:

S1, weighing zirconium oxide, silver oxide, zinc oxide, lanthanum oxide, yttrium oxide, cerium oxide and size control agent in proportion, and mixing by ball milling, to obtain ceramic powder;

S2, putting the ceramic powder into a mold and pre-pressing the ceramic power to obtain an antibacterial denture porcelain block precursor, wherein the pre-pressing pressure is 5 MPa to 50 MPa and the pressure holding time is 10 seconds to 60 seconds; and S3, performing cold isostatic pressing on the antibacterial denture porcelain block precursor, the pressure of the cold isostatic pressing is 100 MPa to 300 MPa and the pressure holding time is 60 seconds to 600 seconds; then performing the pre-sintering on the antibacterial denture porcelain block precursor, the temperature of the pre-sintering is 800° C. to 1000° C., a heating rate is 10° C./min and a temperature holding time is 1 hour to 5 hours; finally, performing the high-temperature sintering in the magnetic field strength of 8T, the of the pre-sintering is 800° C. to 1000° C., with the heating rate of 10° C./min and the temperature holding time of 1 hour to 5 hours; finally, performing the high-temperature sintering on the antibacterial denture porcelain block precursor, the temperature of the high-temperature sintering is 1400° C. to 1550° C., with the heating rate of 1° C./min and the temperature holding time of 1 hour to 5 hours, to obtain the zirconia-based antibacterial denture material.

Comparative Examples 1 to 6

The raw material components and preparation processes in Comparative Examples 1 to 6 are substantially the same as those in Embodiment 3. The difference is that in Comparative Examples 1-6, the components: nanosized silver oxide, nanosized zinc oxide, nanosized lanthanum oxide, and nanosized yttrium oxide, cerium oxide and calcium silicate are not added in sequence.

Testing and Evaluation

The antibacterial properties and bending strength of the zirconia-based antibacterial denture materials in Embodiments 1 to 8 and Comparative Examples 1 to 6 were tested.

Antibacterial performance measurement: putting the test sample and blank control sample into sterilized petri dishes respectively, taking 100 µL of bacterial suspension by a micro-sampler and dropping the bacterial suspension on the surface of each sample, and making three parallel samples for each group. Using a sterile tweezers to pick up the polyethylene film and cover it on the surface of each sample; laying it flat without any bubbles to make the bacterial solution evenly contact the surface of the sample; covering the plate and contact culturing it for 24 hours in an environment of (37±1°) C. and a relative humidity of 90% under natural light or humid and dark conditions; for the samples after contact culture, using 20 mL of physiological saline eluent, repeatedly wash the sample and covering film three times (using tweezers to pick up the film and rinsing); mixing the eluate thoroughly evenly, diluting 10 times to obtain appropriate colony forming units (CFU) count, inoculating 2 plate culture media in parallel for each 100 µL sample solution, and counting the colony after incubation under the conditions of (37±1°) C. and relative humidity of 90%. Finally, calculating the actual number of recovered colonies of the sample according to the dilution factor. The above experiment was repeated three times and the average value was taken. The formula for calculating the antibacterial rate is: R (%)=(A−B)/A×100%, wherein: R represents antibacterial rate (%), A represents the average number of colonies recovered from the blank control sample (CFU/mL), and B represents the average number of recovered colonies (CFU/mL) in the test example. The antibacterial rate results are shown in Table 2.

The flexural strength of each zirconia-based antibacterial denture material was tested according to the method in GBT 6569-2006. The results are shown in Table 2.

properties of the material. In Embodiments 1 to 3, the content of cerium oxide is adjusted, and in Embodiments 3 to 5, the content of nanosized lanthanum oxide is adjusted. It can be seen that, under natural light condition, cerium oxide has a greater influence on the antibacterial effect than lanthanum oxide. Increasing the proportion of cerium oxide is more conducive to improving the antibacterial rate. However, under dark condition, lanthanum oxide has a greater influence on the antibacterial effect than cerium oxide. Increasing the proportion of lanthanum oxide is more conducive to improving the antibacterial rate, and the increase of lanthanum oxide is conducive to the flexural strength of the material. Compared with Embodiment 3, the high-temperature sintering is not carried out under the magnetic field in Embodiment 8, it can be seen that its mechanical properties are reduced. Taking Embodiment 3 as a reference, in Comparative Examples 1 to 6, nanosized silver oxide, nanosized zinc oxide, nanosized lanthanum oxide, nanosized yttrium oxide, cerium oxide, and calcium silicate are respectively not added, it can be seen that nanosized silver oxide, nanosized zinc oxide, nanosized lanthanum oxide and cerium oxide have a synergistic antibacterial effect, while lanthanum oxide, cerium oxide, yttrium oxide and calcium silicate are beneficial to improve the flexural strength of zirconia-based ceramic materials.

The above are only some embodiments of the present application, and the scope of the present application is not limited to this. Any modifications or replacements that can easily be thought of by those skilled in the art based on the disclosure of the present application should be included in the scope of the present application.

What is claimed is:

1. A zirconia-based antibacterial denture material, comprising components with the following mass parts: 75 to 80 parts of zirconium oxide, 2 to 5 parts of nanosized silver

TABLE 2

| | Escherichia coli antibacterial rate (%) | | Staphylococcus aureus antibacterial rate (%) | | |
|---|---|---|---|---|---|
| | natural light condition | dark and moist condition | natural light condition | dark and moist condition | Flexural strength(/Mpa) |
| Embodiment 1 | 88 | 81 | 86 | 82 | 183 |
| Embodiment 2 | 92 | 85 | 93 | 86 | 185 |
| Embodiment 3 | 99 | 88 | 99 | 90 | 187 |
| Embodiment 4 | 97 | 82 | 96 | 84 | 193 |
| Embodiment 5 | 93 | 79 | 94 | 80 | 201 |
| Embodiment 6 | 96 | 84 | 95 | 86 | 174 |
| Embodiment 7 | 98 | 87 | 98 | 90 | 160 |
| Embodiment 8 | 98 | 87 | 98 | 90 | 183 |
| Comparative Example 1 | 65 | 60 | 62 | 59 | 177 |
| Comparative Example 2 | 70 | 64 | 71 | 68 | 181 |
| Comparative Example 3 | 78 | 80 | 85 | 73 | 161 |
| Comparative Example 4 | 98 | 86 | 98 | 89 | 143 |
| Comparative Example 5 | 72 | 75 | 82 | 81 | 153 |
| Comparative Example 6 | 99 | 86 | 97 | 88 | 151 |

Test results of antibacterial properties and flexural strength

Compared with Embodiment 3, the high-temperature sintering process of Embodiment 6 is not carried out under magnetic field conditions. As can be seen from Table 2, the magnetic field is conducive to the improvement of antibacterial performance and flexural strength. Compared with Embodiment 3, the temperature rising of sintering in Embodiment 7 is accelerated, which reduces the mechanical oxide, 3 to 5 parts of nanosized zinc oxide, 1 to 3 parts of nanosized lanthanum oxide, 1 to 3 parts of nanosized yttrium oxide, 1 to 2 parts of cerium oxide, and 1 to 2 parts of size control agent.

2. The zirconia-based antibacterial denture material according to claim 1, wherein the size control agent is calcium silicate.

3. The zirconia-based antibacterial denture material according to claim 1, wherein a ratio of a sum of masses of the silver oxide and the zinc oxide to the mass of the yttrium oxide is between 5 to 0.5 and 5 to 1.

4. The zirconia-based antibacterial denture material according to claim 1, wherein a particle size of the zirconium oxide is less than or equal to 30 nm.

5. A preparation method of a zirconia-based antibacterial denture material, comprising:

weighing zirconium oxide, silver oxide, zinc oxide, lanthanum oxide, yttrium oxide, cerium oxide and size control agent in proportion, and mixing by ball milling, to obtain ceramic powder;

putting the ceramic powder into a mold and pre-pressing the ceramic power to obtain an antibacterial denture porcelain block precursor; and performing cold isostatic pressing, pre-sintering, and high-temperature sintering on the antibacterial denture porcelain block precursor to obtain the zirconia-based antibacterial denture material.

6. The preparation method of the zirconia-based antibacterial denture material according to claim 5, wherein a pressure of the cold isostatic pressing is 100 MPa to 300 MPa, and a pressure holding time is 60 seconds to 600 seconds.

7. The preparation method of the zirconia-based antibacterial denture material according to claim 5, wherein a pressure of the pre-pressing is 5 MPa to 50 MPa, and a pressure holding time is 10 seconds to 60 seconds.

8. The preparation method of the zirconia-based antibacterial denture material according to claim 5, wherein a final temperature of the pre-sintering is 800° C. to 1000° C., a heating rate is 10° C./min to 15° C./min and a temperature holding time is 1 hour to 5 hours.

9. The preparation method of the zirconia-based antibacterial denture material according to claim 5, wherein a final temperature of the high-temperature sintering is 1400° C. to 1550° C., a heating rate is 1° C./min to 10° C./min and a temperature holding time is 1 hour to 5 hours.

10. The preparation method of the zirconia-based antibacterial denture material according to claim 5, wherein a process of the high-temperature sintering is performed in a magnetic field environment.

* * * * *